United States Patent
Kim et al.

(10) Patent No.: US 10,093,995 B2
(45) Date of Patent: Oct. 9, 2018

(54) *LACTOBACILLUS PLANTARUM* AND COMPOSITION COMPRISING THE SAME

(75) Inventors: Bong Joon Kim, Incheon (KR); Heon Woong Jung, Seoul (KR); Kang Pyo Lee, Seoul (KR); Sae Hun Kim, Seoul (KR); Tae Hoon Chun, Seoul (KR); Kwang Woo Hwang, Seoul (KR); Tae Joon Won, Seoul (KR)

(73) Assignee: CJ CHEILJEDANG CORP., Seoul (KR)

( * ) Notice: Subject to any disclaimer, the term of this patent is extended or adjusted under 35 U.S.C. 154(b) by 227 days.

(21) Appl. No.: 13/503,800

(22) PCT Filed: Oct. 27, 2010

(86) PCT No.: PCT/KR2010/007431
§ 371 (c)(1),
(2), (4) Date: Apr. 24, 2012

(87) PCT Pub. No.: WO2011/052996
PCT Pub. Date: May 5, 2011

(65) Prior Publication Data
US 2012/0208260 A1    Aug. 16, 2012

(30) Foreign Application Priority Data
Oct. 28, 2009 (KR) .................. 10-2009-0102822

(51) Int. Cl.
| | | |
|---|---|---|
| *C12R 1/25* | (2006.01) | |
| *C12R 1/225* | (2006.01) | |
| *C12N 1/20* | (2006.01) | |
| *A61K 35/74* | (2015.01) | |
| *A61K 35/747* | (2015.01) | |

(52) U.S. Cl.
CPC .............. *C12R 1/25* (2013.01); *A61K 35/747* (2013.01)

(58) Field of Classification Search
None
See application file for complete search history.

(56) References Cited

U.S. PATENT DOCUMENTS

| | | | | |
|---|---|---|---|---|
| 5,948,651 | A * | 9/1999 | Doherty .............. | C08B 37/0033 435/101 |
| 6,761,885 | B1 * | 7/2004 | Hakansson .......... | A61K 35/744 424/430 |
| 6,977,086 | B1 * | 12/2005 | Barges ................. | A61K 9/0095 424/489 |
| 2004/0047849 | A1 * | 3/2004 | Hsu et al. ................. | 424/93.45 |
| 2005/0053694 | A1 * | 3/2005 | Byun et al. ................ | 426/49 |
| 2006/0088513 | A1 * | 4/2006 | Inoue ................... | A23C 9/1234 424/93.45 |
| 2006/0094056 | A1 * | 5/2006 | Chappell .............. | G01N 33/564 435/7.1 |

FOREIGN PATENT DOCUMENTS

| | | | | |
|---|---|---|---|---|
| WO | WO 2007108763 A1 * | 9/2007 | .......... | A61K 35/747 |
| WO | WO-2007108763 A1 * | 9/2007 | .......... | A61K 35/747 |

OTHER PUBLICATIONS

Kwon, C.W. (KR2001000390, English Abstract; 2001).*
Pochard et al., "Lactic acid bacteria inhibit TH2 cytokine production by mononuclear cells from allergic patients," Journal Allergy and Clinical Immunology, vol. 110, No. 4, pp. 617-623 (2002).*
Hirose et al., The Journal of Nutrition, vol. 136, No. 12, pp. 3069-3073; 2006).*
Kwon, C.W. (KR2001000390, English Abstract; 2001); of record.*
Pochard et al., "Lactic acid bacteria inhibit TH2 cytokine production by mononuclear cells from allergic patients," Journal Allergy and Clinical Immunology, vol. 110, No. 4, pp. 617-623 (2002); of record.*
Hirose et al., The Journal of Nutrition, vol. 136, No. 12, pp. 3069-3073; 2006); of record.*
Pochard et al., Journal Allergy and Clinical Immunology, vol. 110, No. 4, pp. 617-623 ( 2002) of record.*
Pochard et al., Journal Allergy and Clinical Immunology, vol. 11 O, No. 4, pp. 617-623 (2002) of record.*
Rymarchyk et al., Immunology, vol. 125, pp. 331-343 (2008).*
Morelli, L., Current Issues in Intestinal Microbiology, vol. 1, No. 2, pp. 59-67 (2000).*
Pochard et al., Journal Allergy and Clinical Immunology, vol. 11 O, No. 4, pp. 617-623 (2002) (of record).*
Rymarchyket al., Immunology, vol. 125, pp. 331-343 (2008) (of record).*
Pochard et al., Journal Allergy and Clinical Immunology, vol. 110, No. 4, pp. 617-623; 2002 (of record).*
Lee et al., "Evaluation of probiotic characteristics of newly isolated *Lactobacillus* spp.: Immune modulation and longevity", International J. of Food Microbiology, 2011, vol. 148, pp. 80-86.
Won et al., "Immunomodulatory activity of Lactobacillus strains isolated from fermented vegetables and infant stool", Can. J. Physiol. Pharmacol., 2011, vol. 89, pp. 429-434.
Chungnam Research Institute Research Report filed in KIPO for App. No. 10-2009-0102822 (filed Sep. 7, 2011) with summary in English Translation of Korean response to the Office Action dated May 13, 2011.

* cited by examiner

*Primary Examiner* — Soren Harward
*Assistant Examiner* — Paul D. Pyla
(74) *Attorney, Agent, or Firm* — Birch, Stewart, Kolasch & Birch, LLP

(57) ABSTRACT

*Lactobacillus plantarum* CJLP243 (KCTC 11045P), a composition for treating intestinal diseases comprising *Lactobacillus plantarum* CJLP243, and a composition for enhancing immune response comprising *Lactobacillus plantarum* CJLP243.

13 Claims, 6 Drawing Sheets

Specification includes a Sequence Listing.

LACTOBACILLUS PLANTARUM AND COMPOSITION COMPRISING THE SAME

CROSS-REFERENCE TO RELATED APPLICATIONS

The present application is a 35 U.S.C. 371 National Stage Application of International Application No. PCT/KR2010/006916, International Filing Date: Oct. 27, 2010, which claims priority under 35 U.S.C. § 119(a) to Korean Application No. 10-2009-0102822, Filing Date: Oct. 28, 2009, each of which are incorporated herein by reference in its entirety.

TECHNICAL FIELD

The present invention relates to novel *Lactobacillus plantarum* and a composition comprising the same, and more particularly, to novel *Lactobacillus plantarum* for preventing or treating intestinal diseases and immune diseases and a composition comprising the same.

BACKGROUND ART

Lactic acid bacteria found in Korean traditional fermented food, e.g., *kimchi*, inhabit the digestive system of a human body and decompose fibrous materials and complex proteins into important nutrients. Viable microorganisms like lactic acid bacteria are beneficial to gastrointestinal tracts of hosts such as animals including humans due to them improving intestinal microorganism environments of the hosts and are referred to as probiotics. Probiotics are required to have excellent acid resistance and bile resistance, and strong adhesion to intestinal epithelial cells since they need to be orally administered, reach the small intestine and adhere to the surface of the small intestine in order to be effective as probiotics.

*Lactobacillus* sp. lactic acid bacteria are probiotics widely found in Korean traditional fermented food such as Kimchi. *Lactobacillus* sp. microorganisms produce lactic acid under homo-fermentation or hetero-fermentation and are widely found in intestinal tracts of animals including humans, and in fermentation of dairy products and vegetables. *Lactobacillus* sp. microorganisms maintain an acidic pH balance to suppress propagation of hazardous bacteria such as *E. coli* or *Clostridium* and relieve diarrhea and constipation. *Lactobacillus* sp. microorganisms also synthesize vitamins, have anti-cancer activities, and reduce serum cholesterol. Acidophillin produced by *lactobacillus* is known to inhibit the growth of *shigella, salmonella, staphylococcus, E. coli*, or the like. Acidophillin also suppresses the propagation of causative microorganisms of diarrhea and normalizes intestinal flora to prevent diarrhea (Michael and Philippe, Probiotics and prebiotics: Effects on diarrhea, The journal of nutrition, Volume 137, March 2007, pages 803S-811S; Roberfroid, Prebiotics and probiotics: Are they functional foods?, American journal of clinical nutrition, Volume 71, June 2000, pages 1682S-1687S).

Based on the *Lactobacillus* sp. microorganism's functions as stated above, research into *Lactobacillus* sp. microorganism as probiotics and livestock feed is being vigorously conducted. Bacterial diarrhea in livestock causes mortality and a reduction in the rate of weight gain. Thus, a method of adding antibiotics to livestock feed has been widely used in order to prevent bacterial diarrhea and increase the productivity of livestock. However, due to the appearance of antibiotic resistant bacteria and remaining antibiotics in the livestock, the use of antibiotics has been limited and organic methods of raising livestock have been recommended (Korean Patent Publication No. 1998-78358)(McEwen and Fedorka-Cray, Antimicrobial use and resistance in animals, Clinical infectious Diseases, Volume 34, June 2002, pages S93-S106).

In addition, lactic acid bacteria such as *Lactobacillus* sp. microorganism are known to have immune response-enhancing effects. As such, research on the mechanism of effects of lactic acid bacteria on immune response-enhancing effects has been conducted. Even though specific mechanisms have not yet been revealed, it is known that lactic acid bacteria are orally administered and inhabit the intestines to influence the intestinal immune system. For example, the intake of lactic acid bacteria via yogurt is known to increase antibiotic activities of lymphocytes of Peyer's patches. Lactic acid bacteria are known to enhance IgA response according to research into animals and humans. In addition, the immune system representing resistance in the body against external microbial pathogens is divided into innate immunity and adaptive immunity, both of which are influenced by lactic acid bacteria. According to the innate immunity of the intestinal immune system, the lactic acid bacteria are known to prevent and kill pathogens thereby having a function of maintaining healthy conditions against infection. Innate immune reaction plays an important role in suppressing the increase of the number of external pathogens at an early stage of an infection. Additionally, innate immune reaction delivers antigens and co-stimulatory molecules, thereby inducing the activation of the adaptive immunity subsequent to the innate immune system. Representative immunocytes related to the innate immune reaction includes NK cells, neutrophiles, macrophages, and dendritic cells (Fearon D T, Locksley R M, Science 1996, 272:50-53, The instructive role of innate immunity in the acquired immune response). Adaptive immunity substantially induces the removal of external pathogen when a subject is infected, and the immunocytes corresponding to adaptive immunity include T lymphocytes and B lymphocytes. Accordingly, physical resistance to external pathogens may depend on the enhancement of the activity of adaptive immunity (Gowans J L., Immunology Today. 1996 June; 17(6):288-91, The lymphocyte—a disgraceful gap in medical knowledge).

According to the adaptive immunity, macrophages that decompose antigens to bring them into contact with T lymphocytes are activated to increase the production of a variety of cytokines, particularly, interleukin, IL-12, and IL-18. In this regard, some components of the cell walls of lactic acid bacteria activate NF-κB and STAT signal transfers in the macrophages to increase the production of the cytokines. In addition, it is known that lactic acid bacteria increase the production of IL-12, IL-18, and TNF-α in antigens presenting cells such as dendritic cells often found in lymphatic nodes and mucosa of the digestive system. Furthermore, lactic acid bacteria are known to increase the expression of a surface molecule in dendritic cells that activate T lymphocytes such as MHC class II and B7-2 (Cross et. al., Anti-allergy properties of fermented foods: an important immunoregulatory mechanism of lactic acid bacteria?, International Immunopharmacology, Volume 1, May 2001, pages 891-901).

Much research on the interrelation between *Lactobacillus* sp. microorganisms and immune reactions has been carried out. Specifically, some *Lactobacillus* sp. (e.g. *L. fermentum*) is known to enhance an antigen-specific immune reaction, and thus its use as an adjuvant in bacteria (e.g. diphtheria, tetanus) or virus (e.g. influenza, polio) vaccines was tried (de Vrese et al., 2005; Olivares et al., 2007; West et al., 2008). Immune-enhancing effects of *Lactobacillus* sp. microorganism are considered to result from the enhanced activity of Th1-type cytokine-producing T lymphocyte by specific *Lactobacillus* sp. microorganisms, which effectively induce the growth of general immune cells and the activity of T cells or B cells in adaptive immunity (Mohamadzadeh et al., Lactobacilli activate human dendritic cells that skew T cells toward T helper 1 polarization, Proc Natl Acad Sci USA. 2005 22; 102(8):2880-2885). in order to measure the enhanced activity of T lymphocyte, the study of measuring the amount of produced IFN-γ is actively performed in recent years (Shida et al., 2006; Foligne et al., 2007). It is known that the induction of general immune cell growth may prevent or treat digestive tract (intestinal) infection (Jain S, Yadav H, Sinha P R. Probiotic dahi containing *Lactobacillus casei* protects against *Salmonella enteritidis* infection and modulates immune response in mice. J Med Food, 2009 June; 12(3):576-83.), genitourinary infection (Zarate G, Santos V, Nader-Macias M E. Protective effect of vaginal *Lactobacillus paracasei* CRL 1289 against urogenital infection produced by *Staphylococcus aureus* in a mouse animal model. Infect Dis Obstet Gynecol. 2009; 2009: 48358. Epub 2007 Mar. 29.), respiratory infection (Yasuda Y, Matsumura Y, Kasahara K, Ouji N, Sugiura S. Mikasa K, Kita E. Microbial exposure early in life regulates airway inflammation in mice after infection with *Streptococcus pneumoniae* with enhancement of local resistance. Am J Physiol Lung Cell Mol Physiol. 2009 Sep. 25 [Epub ahead of print]), *helicobacter* infection (Boyanova L, Stephanova-Kondratenko M, Mitov I. Anti-*Helicobacter pylori* activity of *Lactobacillus delbrueckii* subsp. *bulgaricus* strains: preliminary report. Lett Appl Microbiol. 2009 May; 48(5):579-84. Epub 2009 Mar. 9.), and allergic reactions (Ouwehand A C, Nermes M, Collado M C. Rautonen N, Salminen S. Isolauri E. Specific probiotics alleviate allergic rhinitis during the birch pollen season. World 3 Gastroenterol. 2009 Jul. 14; 15(26):3261-8).

T lymphocytes control adaptive immunity which may be classified into a Th1 response as cellular immunity and a Th2 response as humoral immunity. Th1 and Th2 responses produce different cytokines in the antigen presenting cells. In the Th1 response, the production of IL-2, IL-12, IL-18, interferon-γ (IFN-γ is dominant. In the Th2 response, the production of PGE2, IL-4, and IL-10 is dominant. The Th1 and Th2 responses are required to be balanced. If the Th1 and Th2 responses are not balanced, a variety of immune diseases occur. Th1 cells mainly fight with pathogens, but Th2 cells are mainly related to allergies and inflammatory responses. When the Th1 and Th2 responses are in normal conditions, Th2 cells protect the human body from dust and undesired materials. However, if the Th2 cells excessively respond, the production of IgE antibodies increases, thereby causing allergic responses to proteins that are not hazardous to the human body, such as pollen and food. Thus, the ratio of Th1 and Th2 responses should be balanced. Excessive or insufficient response of one of them causes diseases. In addition, continuous secretion of cortisol due to continuous stress decreases Th1 response and increases Th2 response, thereby causing cancer, atopic diseases, allergies, and autoimmune diseases (Elenkov and Chrousos, Stress hormones, Th1/Th2 patterns, pro/anti-inflammatory cytokines and susceptibility to disease, Trends in Endocrinology and Metabolism, Volume 10, November 1999, pages 359-368).

According to in vivo experiments, lactic acid bacteria increase the production of IL-2 and IFN-γ that are Th1 cytokines in T lymphocytes and suppress the production of IL-4 and IL-5 that are Th2 cytokines (Matsuzaki et. al., The effect of oral feeding of *Lactobacillus casei* strain Shirota on immunoglobulin E production in mice, Journal of Dairy Science, Volume 81, January 1998, pages 48-53). Meanwhile, IL-12 and IL-18 are important cytokines to differentiate Th0 lymphocytes into Th1 lymphocytes and produced in macrophages or dendritic cells. It is known that the production of IL-12, IL-18 and IFN-α increases depending upon the concentration of lactic acid bacteria, when splenocytes or macrophages are treated with lactic acid bacteria during the culturing. As such, lactic acid bacteria increase the production of IL-12, IL-18 and IFN-α in macrophages, thereby promoting the differentiation of Th0 into Th1 and inducing the formation of IFN-γ and thus lactic acid bacteria play a role in balancing the Th1/Th2 in a Th2-response primed state (Cross et. al., Anti-allergy properties of fermented foods: an important immunoregulatory mechanism of lactic acid bacteria?, International Immunopharmacology, Volume 1, May 2001, pages 891-901). Thus, lactic acid bacteria are known to prevent and treat cancers, atopic diseases, allergies, and autoimmune diseases induced by the Th1/Th2 imbalance caused by the over-response of Th2.

DISCLOSURE OF INVENTION

Technical Problem

While searching for novel lactic acid bacteria having excellent immune-enhancing activities in comparison with the conventional lactic acid bacteria, the present inventors isolated and identified *Lactobacillus* sp. bacteria isolated from Korean traditional fermented food.

Thus, the present invention provides *Lactobacillus* sp. bacteria strains having excellent effects on enhancing immune response, particularly, excellent activities for promoting the production of IFN-γ, a Th1-type cytokine, inducing the proliferation of general immune cells, and countering Th1/Th2 imbalance caused by an over-response of Th2, as well as having excellent acid and bile resistance and strong adhesion to intestinal epithelial cells constituting basic properties of probiotics.

The present invention also provides a composition for preventing or treating intestinal diseases, comprising *Lactobacillus* sp. bacteria strains.

The present invention also provides a composition for enhancing immune response, comprising *Lactobacillus* sp. bacteria strains.

Solution to Problem

According to an aspect of the present invention, there is provided *Lactobacillus plantarum* CJLP243 (deposited in Korean Culture Center of Microorganisms (KCCM), Deposition date: Oct. 14, 2009, Deposition No.: KCCM11045P).

According to another aspect of the present invention, there is provided a composition for preventing or treating intestinal diseases, comprising *Lactobacillus plantarum* CJLP243.

According to an aspect of the present invention, there is provided a composition for enhancing immune response, comprising *Lactobacillus plantarum* CJLP243.

Hereinafter, the present invention will be described more fully with reference to the accompanying drawings, in which exemplary embodiments of the invention are shown.

*Lactobacillus plantarum* CJLP243 according to an aspect of the present invention is a novel strain of *Lactobacillus plantarum* isolated and identified from Korean traditional fermented food. The Korean traditional fermented food may be kimchi, fermented vegetables, soybean paste, soy sauce, chungkookjang, fermented fish, or the like, but is not limited thereto.

A result of a 16S rRNA base sequence assay for identifying and classifying *Lactobacillus plantarum* showed that *Lactobacillus plantarum* CJLP243 had the highest homology (99.9%) with a *Lactobacillus plantarum* standard strain (*Lactobacillus plantarum* NBRC15891$^T$, GenBank accession number AB326351) and showed the closest molecular phylogenetic relationship with *Lactobacillus plantarum*. Thus, the said microorganism was identified as *Lactobacillus plantarum*, named *Lactobacillus plantarum* CJLP243, and deposited in the Korean Culture Center of Microorganisms (KCCM) on Oct. 14, 2009 (Deposition No.: KCCM11045P). The base sequence of a 16S rRNA gene of *Lactobacillus plantarum* CJLP243 is shown at SEQ ID NO: 1 in the sequence list attached hereto.

*Lactobacillus plantarum* CLJP243 is a gram-positive bacterium and a facultative anaerobe that may grow in both aerobic and anaerobic conditions, does not produce spores, does not have motility, and has a rod shape. Specific morphological and physiological properties of *Lactobacillus plantarum* CLJP243 have been analyzed according to conventional methods known in the art and are shown in Table 1 below.

TABLE 1

| Morphological, physiological, and biochemical properties | Results |
| --- | --- |
| Morphology | Rod |
| Motility | − |
| Spore | − |
| Catalase | − |
| Homo-hetero fermentation | facultative hetero fermentation |
| Proliferation at 10° C. | + |
| Proliferation at 42° C. | + |
| Proliferation at 7% NaCl | + |
| Proliferation at 10% NaCl | − |
| Proliferation at pH 3.8 | + |
| Proliferation in anaerobic conditions | + |
| Production of $CO_2$ using glucose | − |
| Sugar-fermentation | |
| Glycerol | − |
| Erythritol | − |
| D-arabinose | − |
| L-arabinose | + |
| Ribose | + |
| D-xylose | − |
| L-xylose | − |
| Adonitol | − |
| xyloside | − |
| Galactose | + |
| D-glucose | + |
| D-fructose | + |
| D-mannose | + |
| L-sorbose | − |
| Rhamnose | + |
| Dulcitol | − |
| Inositol | − |
| Mannitol | + |
| Sorbitol | + |
| D-mannoside | + |
| D-glucoside | + |
| Glucosamine | + |
| Amygdalin | + |
| Alutin | + |
| Esculin | + |
| Salicin | + |
| Cellobiose | + |
| Maltose | + |
| Lactose | + |

TABLE 1-continued

| Morphological, physiological, and biochemical properties | Results |
| --- | --- |
| Melibiose | + |
| Sacarose | + |
| Trehalose | + |
| Inulin | + |
| Melizitose | + |
| D-raffinose | + |
| Amidon | − |
| Glycogen | − |
| Xylitol | − |
| Gentiobiose | − |
| D-turanose | − |
| D-lyxose | − |
| D-tagatose | − |
| D-fucose | − |
| L-fucose | − |
| D-arabitol | − |
| L-arabitol | − |
| Gluconate | − |
| 2-gluconate | − |
| 5-gluconate | − |

+: positive
−: negative

In order to stably preserve *Lactobacillus plantarum* CJLP243 for a long period of time, the strains may be preserved by dispensing them in a preservation solution prepared by mixing water and glycerol and storing the dispension at −70° C., or by suspending them in sterilized 10% skim milk and lyophilizing the suspension.

In addition, *Lactobacillus plantarum* CJLP243 is a probiotic that is effective for relieving intestinal disorders and enhancing immune response that are general effects of lactic acid bacteria.

In this regard, a probiotic is a viable microorganism beneficial to gastrointestinal tracts of hosts such as animals including humans by improving intestinal environments. Probiotics, which are living microorganisms having probiotic activities in a single or complex strain, are beneficial to intestinal flora when administered to humans or animals in a dried or fermented form. The probiotic microorganism should not be influenced by gastric juice and bile, and is required to be viable in the intestine after passing through the stomach, inhabits the intestine, and is beneficial to intestinal flora of a host. Thus, the probiotic microorganism needs to have excellent acid resistance and bile resistance, and strong adhesion to intestinal epithelial cells. In addition, the probiotic microorganism is required to be stable. In this regard, a gelatin liquefaction test, a phenylalanine deaminase test, an ammonia formation test, a hemolysis test, or the like are conducted. *Lactobacillus plantarum* CJLP243 according to the present embodiment is negative for the gelatin liquefaction test, the phenylalanine deaminase test, and the ammonia formation test, and shows α-hemolysis indicating that *Lactobacillus plantarum* CJLP243 is not a pathogen (refer to Example 4), has excellent acid resistance and bile resistance, and shows strong adhesion to intestinal epithelial cells (refer to Examples 2 and 3).

*Lactobacillus plantarum* CJLP243 may have excellent effects on relieving intestinal disorders due to excellent acid resistance and bile resistance, and shows strong adhesion to intestinal epithelial cells.

Thus, another aspect of the present invention provides a composition for preventing or treating intestinal diseases, comprising *Lactobacillus plantarum* CJLP243.

The composition for treatment of intestinal diseases comprising *Lactobacillus plantarum* CJLP243 may be applied to prevent or treat intestinal diseases of mammals including humans, for example, livestock including cows, horses, and pigs. Such intestinal diseases include intestinal infections b bacteria hazardous to intestinal environments and inflammatory bowel diseases, for example, infectious diarrhea caused by pathogenic microorganisms (*E. coli, salmonella,* and *clostridium*), gastroenteritis, inflammatory bowel diseases, psychogenic enteritis syndrome, overgrowth of microorganisms in the small intestine, diarrhea, or the like, bat is not limited thereto. *Lactobacillus plantarum* CJLP243 contained in the composition for treating intestinal diseases may be live or dead bacteria, and preferably live bacteria. In general, the live bacteria treat or relieve general symptoms caused by abnormal fermentation in the intestinal flora, inhabit the intestinal tracts to prevent hazardous bacteria from adhering to the intestinal tracts in humans and animals, and produce lactic acid to lower the intestinal pH, thereby suppressing proliferation of hazardous bacteria. In addition, the administered live bacteria produce peroxides with bacteriocin to suppress the proliferation of hazardous bacteria and help the activity of intestinal villi to absorb nutrients. In addition. live bacteria may produce materials assisting absorption and utilization of nutrients, improve livestock feed requirements, and produce materials neutralizing toxic materials produced by pathogens.

The composition for preventing or treating the intestinal diseases may be orally administered, but the method of administering the composition is not limited thereto. The dose may vary according to types of the intestinal disease, the degree of seriousness, age, gender, and ethnicity of patients, and purposes of the treatment or prevention. In general, 10 million to 100 billion bacteria may be administered to an adult.

In addition, *Lactobacillus plantarum* CJLP243 has excellent effects on enhancing immune response as well as effects on relieving intestinal disorders when compared to conventional lactic acid bacteria. *Lactobacillus plantarum* CJLP243 is found to promote the production of IFN-γ, Th-1 type cytokines, thereby inducing the enhancement of Th-1 type immunization. Effects on enhancing in response of *Lactobacillus plantarum* CJLP243 will now be described in more detail.

When immune cells isolated from a spleen of a mouse were treated with *Lactobacillus plantarum* CJLP243, they activated the growth of Th2 response-induced general immune cells (Example 5), and increased the production of IFN-γ, Th1-type cytokines (Example 6). The activation of immune cell growth and the enhancing effects of Th1-type immune reaction are found to be significantly advantageous over other conventional lactic acid bacteria such as *Lactobacillus rhamnosus* GU (KCTC 5033). In addition, when *Lactobacillus plantarum* CJLP243 was orally administered to mice for 8 weeks. it was shown that the production of IFN-γ and IL-2, a Th-1 type cytokine, was increased and the growth of T cell, CD4 T cell, and CD8 T cell were all increased. Thus, it can be said that *Lactobacillus plantarum* CJLP243 produces such a large quantity of IFN-γ as to promote Th1-type response, thereby not only enhancing, general immunity but also regulating the immune imbalance of Th1/Th2.

It is known that an increase in general immune cells, specifically T cells including CD4 T cells and CD-8 T cells, enhances immunity to be effective for preventing or treating digestive tract (intestinal) infection, urogenital infection, respiratory infection, *helicobacter* infection or allergic reactions (digestive tract (intestinal) infection; Jain S, Yadav H, Sinha P R. Probiotic dahi containing *Lactobacillus casei* protects against *Salmonella enteritidis* infection and modulates immune response in mice. J Med Food. 2009 June; 12(3):576-83, urogenital infection; Zarate G, Santos V, Nader-Macias M E. Protective effect of vaginal *Lactobacillus paracasei* CRL 1289 against urogenital infection produced by *Staphylococcus aureus* in a mouse animal model. Infect Dis Obstet Gynecol. 2009; 2009: 48358. Epub 2007 Mar. 29, respiratory infection; Yasuda Y, Matsumura Y, Kasahara K, Ouji N, Sugiura S, Mikasa K, Kita E. Microbial exposure early in life regulates airway inflammation in mice after infection with *Streptococcus pneumoniae* with enhancement of local resistance. Am J Physiol Lung Cell Mol Physiol. 2009 Sep. 25. [Epub ahead of print]; or *helicobacter* infection (Boyanova L, Stephanova-Kondratenko M, Mitov I. Anti-*Helicobacter pylori* activity of *Lactobacillus delbrueckii* subsp. *bulgaricus* strains: preliminary report. Lett Appl Microbiol. 2009 May; 48(5):579-84. Epub 2009 Mar. 9.) and allergic reactions (Ouwehand A C, Nermes M, Collado M C, Rautonen N, Salminen S, Isolauri E. Specific probiotics alleviate allergic rhinitis during the birch pollen season. World J Gastroenterol. 2009 Jul. 14; 15(26):3261-8). Therefore, the experimental results show that *Lactobacillus plantarum* CJLP243 is effective for preventing or treating digestive tract (intestinal) infection, urogenital infection, respiratory infection, *helicobacter* infection or allergic reaction, due to the enhanced general immunity resulting from the activation of T cell growth.

Recently, it has been reported that Th2 cells relatively increase in peripheral blood and skin lesions in patients having atopic dermatitis (Miraglia et. at, Immune dysregulation in atopic dermatitis, Allergy and Asthma Proceedings, Volume 27, November-December 2006, pages 451-455). Thus, a Th1/Th2 imbalance caused by over-response of Th2 induces diseases such as atopic dermatitis. In addition, as described above, over-response or insufficient response of Th1 or Th2 causes an outbreak of diseases. If the Th1 response decreases and the Th2 response increases, cancers, atopic diseases, allergies, and autoimmune diseases are known to be caused (Elenkov and Chrousos, Stress hormones, Th1/Th2 patterns, pro/anti-inflammatory cytokines and susceptibility to disease, Trends in Endocrinology and Metabolism, Volume 10, November 1999, pages 359368). Thus, it is expected that *Lactobacillus plantarum* CJLP243 may be applied not only to atopic diseases and allergies but also to cancers and autoimmune diseases since *Lactobacillus plantarum* CJLP243 controls a Th1/Th2. imbalance by promoting Th1-type reactions.

Another aspect of the present invention provides a composition for enhancing immune response, comprising *Lactobacillus plantarum* CJLP243. The composition for enhancing immune response is effective for reinforcing immune response since *Lactobacillus plantarum* CJLP243 is a lactic acid bacterium that is effective for enhancing immune response as described above. In particular, as proven by the examples described below, *Lactobacillus plantarum* CJLP243 is effective, for activating growth of general immune cells, and thus the composition for enhancing immune response is effective for preventing or treating digestive tract (intestinal) infection, urogenital infection, respiratory infection, *helicobacter* infection and allergic reaction. Furthermore, the composition for enhancing immune response is effective for preventing or treating the diseases caused by a TH1/Th2 imbalance, since CJLP243 is effective for promoting Th1 response. Thus, the composition for enhancing immune response may be effectively used for preventing or treating atopic disease, allergies, cancer and autoimmune disease. The autoimmune diseases include asthma, hay fever, and the like.

The composition for enhancing immune response may be orally administered, but the method of administering the composition is not limited thereto. The dose may vary according to the type of disease, immunity to which need to be enhanced, the degree of seriousness, age, gender, and ethnicity of patients, and purposes of the treatment or prevention. In general, 10 million to 100 billion bacteria may be administered to an adult.

The composition for preventing or treating intestinal diseases, comprising *Lactobacillus plantarum* CJLP243 and the composition for enhancing immune response comprising *Lactobacillus plantarum* CJLP243, use lactic acid bacteria whose safety is proven, sand thus the compositions may be applied to pharmaceuticals, functional food, cosmetics, livestock feed, or additives to livestock feed, without any concern about side effects.

If the composition is used as pharmaceuticals, the composition may be formulated in pharmaceutical formulations that are commonly used in the art. The pharmaceuticals may be formulations for oral administration such as liquids, suspensions, powder, granules, tablets, capsules, pills, or extracts.

While the composition is formulated, pharmaceutically acceptable compatible excipients or additives may be added to the formulations. The formulation for oral administration may include at least one selected from the group consisting of a diluent, a lubricant, a binder, a disintegrant, a sweetener, a stabilizer, and a preservative, as the excipient, and at least one selected from the group consisting of a flavoring agent, a vitamin, and an antioxidant, as an additive.

The excipient and the additive may be any pharmaceutically acceptable material. In particular, the diluent may be lactic acid, corn starch, soybean oil, microcrystalline cellulose, or mannitol, the lubricant may be magnesium stearate or talc, and the binder may be polyvinyl pyrrolidone or hydroxypropylcellulose. In addition, the disintegrants may be calcium carboxymethylcellulose, sodium starch glycolate, polacrilin potassium, or crospovidone, the sweetner may be white sugar, fructose, sorbitol, or aspartame, the stabilizer may be sodium carboxymethylcellulose, β-cyclodextrin, white wax, or xanthan gum, and the preservative may be methyl paraoxybenzoate, propyl paraoxybenzoate, or potassium sorbate.

In addition to the above substances, a natural flavor such as plum flavor, lemon flavor, pineapple flavor, or herb flavor, a natural fruit juice, a natural colorant such as chlorophylin or flavonoid, a sweetening agent such as fructose, honey, sugar alcohol, or sugar, or an acidifier such as citric acid or sodium citrate, or combinations thereof may be added to the formulation in order to improve taste.

This method of formulation, and excipients and additives for the formulation are described in detail in Remington's Pharmaceutical Sciences (19th ed., 1995).

The composition may be used as food. The food may include not only functional food but also everyday food. The composition used as functional food may be formulated into a variety of formulations that are commonly used in the art with sitologically acceptable excipients or additives. The functional food may be powder, granules, tablets, capsules, suspensions, emulsions, syrups, liquids, extracts, tea, jelly, drinks, or the like. Any sitologically acceptable excipients or additives that are commonly used in the art may be used.

Due to its effectiveness for preventing or treating atopic diseases, the composition may be used in cosmetics. The composition used in cosmetics may be formulated in a variety of formulations that are commonly used in the art. During the preparation of formulations, excipients or additives that are acceptable for cosmetics may be added thereto.

The composition may be used as livestock feed or livestock feed additives.

If the composition is used as a livestock feed additive, the composition may be a liquid with high concentration ranging from 20 to 90% or may be prepared as powder or granules. The livestock feed additive may include at least one selected from the group consisting of an organic acid such as citric acid, fumaric acid, adipic acid, lactic acid, or malic acid, phosphate salt such as sodium phosphate, potassium phosphate, acidic pyrrophosphate, or polyphosphate (polymerized phosphate), and a natural antioxidant such as polyphenol, catechin, α-tocopherol, rosemary extract, vitamin C, green tea extract, licorice extract, chitosan, tannic acid, or phytic acid. The composition used as livestock feed may be formulated in a variety of formulations that are commonly used in the art with ingredients commonly used in livestock feed.

The livestock feed additive and livestock feed may include grains such as powdered or pulverized wheat, oats, barley, corn, or rice; plant protein livestock feed containing rape, bean, or sunflower as a main ingredient; animal protein livestock feed such as blood powder, meat powder, bone powder, or fish powder; sugar; and dairy products such as powdered milk and whey powder. The livestock feed additive and livestock feed may further include nutrient supplements, digestion and absorption assisting agents, growth promoting substances, or the like.

The livestock feed additive alone may be administered to animals or may be combined with another livestock feed additive in edible excipients to be administered. In addition, the livestock feed additive may be administered as a top dressing to the livestock feed or as a mixture with the livestock feed. Alternatively, the livestock feed additive may be orally administered separately from the livestock feed as a separate formulation. If the livestock feed additive is administered separately from the livestock feed, it is combined with pharmaceutically acceptable edible excipients to prepare an immediate release or sustained release formulation. The edible supports may be solid or liquid, such as corn starch, lactose, sucrose, bean flake, peanut oil, olive oil, sesame oil, or propylene glycol. If a solid excipient is used, the livestock feed additive may be in the form of tablets, capsules, powder, troches or lozenges, or a non-dispersed top dressing. If a liquid excipient is used, the livestock feed additive may be in the form of gelatin soft capsules, a syrup suspension, an emulsion, or a solution.

The livestock feed may include organic cereal flour containing protein that is commonly used to satisfy the dietary demand of animals. The protein-containing cereal flour may include corn, bean flour, or corn/bean flour mix.

In addition, the livestock feed additive and livestock feed may include additives such as a preservative, a stabilizer, a wetting agent, an emulsifier, and a solubilizing agent. The livestock feed additive may be added to the livestock feed by infiltration, spraying, and mixing.

The livestock feed or livestock feed additive may be applied to livestock feeds for various animals such as mammals, poultry, and fish. The mammals include pigs, cows, sheep, goats, rodents for experimentation, and pets (e.g., dogs and cats). The poultry includes chicken, turkeys, ducks, geese, pheasants, and quails, and the fish includes trout. However, the livestock is not limited thereto.

Advantageous Effects of Invention

As described above, *Lactobacillus plantarum* CJLP243 according to the present invention is a probiotic having excellent acid resistance, bile resistance, and strong adhesion to intestinal epithelial cells, and thus is effective for relieving intestinal disorders. Furthermore, *Lactobacillus plantarum* CJLP243 is effective for preventing or treating various diseases due to its immune-enhancing effects resulting from promoting the growth of general immune cells including T cells. Particularly, *Lactobacillus plantarum* CJLP243 promotes Th1 response and thus it is effective for treating diseases caused by a Th1/Th2 imbalance due to over-response of Th2. Therefore, *Lactobacillus plantarum* CJLP243 according to the present invention may be applied to a composition for treating intestinal diseases and a composition for enhancing immune response.

BRIEF DESCRIPTION OF DRAWINGS

The above and other features and advantages of the present invention will become more apparent by describing in detail exemplary embodiments thereof with reference to the attached drawings in which.

MODE FOR THE INVENTION

Hereinafter, the present invention will be described in detail with reference to the following examples. However, these examples are not intended to limit the purpose and scope of the invention.

Example 1: Isolation and Identification of *Lactobacillus plantarum* CJLP243 Strains

*Lactobacillus plantarum* CJLP243 strains isolated from kimchi were smeared onto a solid MRS medium (Difco, USA) containing 1.5% agar, and incubated at 37° C. for 24 hours. Colonies that were, proven to be pure were collected using a loop and incubated in a liquid MRS medium (Difco, USA) at 37° C. for 18 to 24 hours.

Then, morphological and physiological properties of *Lactobacillus plantarum* CJLP243 strains were measured using a method reported by Kim et. al. (Kim et. al., *Leuconostoc inhae* sp. nov., a lactic acid bacterium isolated from kimchi, International Journal of Systematic and Evolutional Microbiology, Volume 53, July 2003, pages 1123-1126), and using API50CH and API50CHL kits (Biomerio). The identified morphological and physiological properties of *Lactobacillus plantarum* CJLP243 are listed in Table 1 above.

In addition, a base sequence of a 16S rRNA gene was analyzed to identify and classify lactic acid bacteria. The determination and assay of the base sequence of the 16S rRNA gene were conducted using a method reported by Kim et. al. (Kim et. al., *Leuconostoc kimchii* sp. nov., a new species from *kimchi*. International Journal of Systematic and Evolutional Microbiology, Volume 50, September 2000, pages 1915-1919. As a result, the base sequence of the 16S rRNA gene of *Lactobacillus plantarum* CJLP243 is shown at SEQ ID NO: 1 in the sequence list attached hereto.

As a result et a 16S rRNA base sequence assay, a *Lactobacillus plantarum* CJLP243 strain had the highest homology (99.9%) with a *Lactobacillus plantarum* standard strain (*Lactobacillus plantarum* NBRC15891$^T$, GenBank accession number AB326351), and was identified, named *Lactobacillus plantarum* CJLP243, and deposited in the Korean Culture Center of Microorganisms (KCCM) on Oct. 14, 2009 (Deposition No.: KCCM11045P).

Example 2: Acid Resistance Test in Artificial Gastric Juice and Bile Resistance Test in Artificial Bile for *Lactobacillus plantarum* CJLP243 Strains An acid resistance test in an artificial gastric juice was conducted using an artificial gastric juice prepared using a modified method reported by Kobayashi et. al., (Kobayashi et. al., Studies on biological characteristics of *Lactobacillus*: II. Tolerance of the multiple antibiotic resistance strain, *L. casei* PSR3002, to artificial digestive fluids. Japan Journal of Microbiology. Volume 29, July 1974, pages 691-697). In particular, the artificial gastric juice was prepared by adjusting the pH of a liquid MRS medium to 2.5 using 1N HCl, adding pepsin to a concentration of 1000 unit/ml, and sterilizing the medium.

The *Lactobacillus plantarum* CJLP243 strains isolated and identified in Example 1 and incubated in a liquid MRS medium at 37.degree. C. for 18 hours were centrifuged to precipitate the strains, and washed twice with sterilized saline (0.85% NaCl). Then, the strain suspension was inoculated onto a control medium and the artificial gastric juice to a concentration of about $10^7$ cfu/ml. The number of surviving strains was measured at the beginning of the inoculation and after 3 hours of the inoculation while culturing at 37.degree.C., in which the total number of strains was measured by diluting the strains 10 times with a phosphate-buffered solution (pH 6.8) containing $KH_2PO_4$, $Na_2HPO$, L-cysteine, HCl, Tween 80, and the like.

A bile resistance test in artificial bile was conducted according to a method reported by Casey et. al. (Casey et. al., Isolation and characterization of anti-*Salmonella* lactic acid bacteria from the porcine gastrointestinal tract, Letters in Applied Microbiology. Volume 39, 2004, pages 431-438). The *Lactobacillus plantarum* CJLP243 was incubated in the medium which was prepared by adding 0.3% bile of a bull to the liquid MRS medium used in the acid resistance test above. The strains were inoculated in the same manner as in the acid resistance test above, and the number of surviving strains was measured at the beginning of the inoculation and after 12 and 24 hours of the inoculation.

The acid resistance test and the bile resistance test of *Lactobacillus rhamnosus* GG (KCTC 5033) were conducted in the same manner as in the tests of *Lactobacillus plantarum* CJLP243 for comparison.

Figure 1:
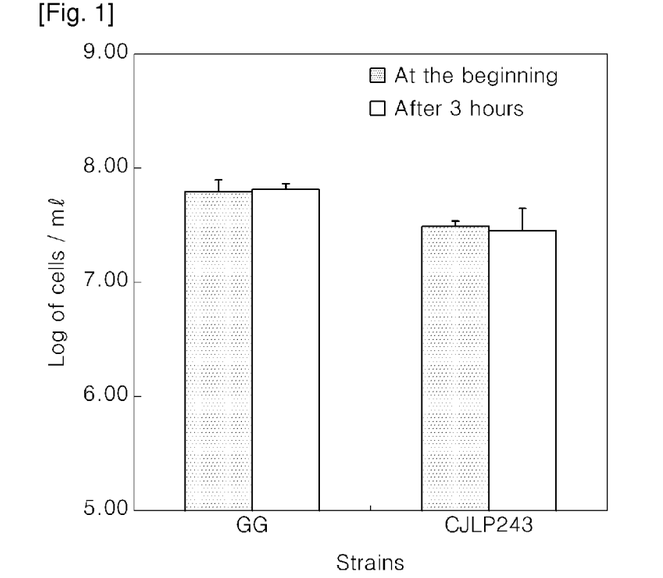
FIG. 1 is a graph illustrating acid resistance of *Lactobacillus plantarum* CJLP243.
Figure 2:
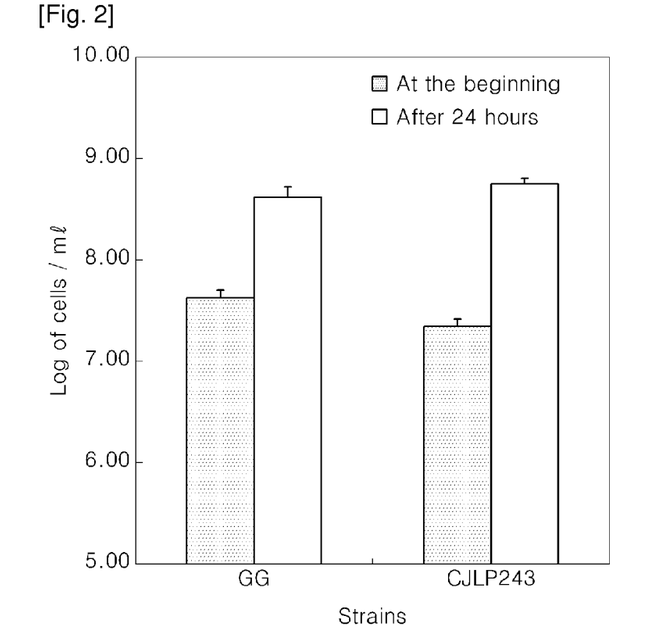
FIG. 2 is a graph illustrating bile resistance of *Lactobacillus plantarum* CJLP243.

The results are shown in FIGS. 1 and 2. FIG. 1 is a graph illustrating acid resistance of *Lactobacillus plantarum* CJLP243, FIG. 2 is a graph illustrating bile resistance of *Lactobacillus plantarum* CJLP243.

According to FIGS. 1 and 2, *Lactobacillus plantarum* CJLP243 had equal or greater acid resistance and bile resistance compared to other lactic acid bacteria. This indicates that *Lactobacillus plantarum* CJLP243 according to the present invention may reach intestines without being affected by gastric juice and inhabit the intestines without being affected by bile.

Example 3: Adhesion of *Lactobacillus plantarum* CJLP243 Strains to Intestinal Epithelial Cells HT-29 was obtained from Korean Cell Line Bank (KCLB) as an animal cell to test adhesion to intestinal epithelial cells, and the test was conducted using methods reported by Kim et. al. (Kim et. al., Probiotic properties of *Lactobacillus* and *Bifidobacterium* strains isolated from porcine gastrointestinal tract, Applied Microbiology and Biotechnology, Volume 74, April 2007, pages 1103-1111) and by Hirano et. al. (Hirano et. al., The effect of *Lactobacillus rhamnosus* on enterohemorrhagic *Escherichia coli* infection of human intestinal cells in vitro, Microbiology and Immunology, Volume 47, 2003, pages 405-109).

HT-29 cells were cultured in a RPMI 1640 (Gibco, USA) medium containing heat inactivated 10% fetal bovine serum (FBS), 1% L-glutamine, penicillin G (100 IU/mL), and streptomycin (100 mg/mL) in the presence of 5% $CO_2$ at 37° C. In order to measure an adhesion ability and an adhesion inhibitory ability, HT-29 cells were divided into a 24-well plate such that the number of HT-29 cells per well was $1.0 \times 10^5$ cell/mL. The HT-29 cells were cultured while altering the culture media every other day until a monolayer was completely formed. The completely formed monolayer of HT-29 cells was washed five times with PBS buffer solution at 25° C., and 0.5 mL of a RPMI 1640 medium without antibiotics was added thereto.

*Lactobacillus plantarum* CJLP243 was suspended in a RPMI medium to a concentration of about $1.0 \times 10^9$ cfu/mL, and the suspension was inoculated into the 24-well plate prepared above and incubated in the presence of 5% $CO_2$ at 37° C. for 2 hours. When the incubation was completed, the 24-well plate was washed three times with the PBS buffer solution while stirring at 200 rpm for 3 minutes in order to remove strains that did not adhere to the well-plate and to identify strains that have an ability to adhere to the cell over the washing. After the washing, 0.2% trypsin-EDTA was added into the wells to isolate the adhered cells. The isolated cells were diluted in peptone water by way of a serial dilution method and smeared on a MRS-agar plate, and then cultured at 37° C. for 24 hours. After the culturing, the number of strains was counted.

Separately, in order to identify partial adhesion, after a cover glass completely sterilized by immersing it in 70% alcohol for one day was attached to the bottom of a petri-dish and HT-29 cells were incubated, the same amount of lactic acid bacteria as used above was added thereto. and then cultured and washed in the same manner as described above. Lactic acid bacteria that were not washed and adhered to the HT-29 cells were dried and stained using Gram staining. The stained bacteria were observed using an optical microscope and the number of strains was measured. The same experiments were conducted using *Lactobaillus rhamnosus* GG (KCTC 5033).

Figure 3:
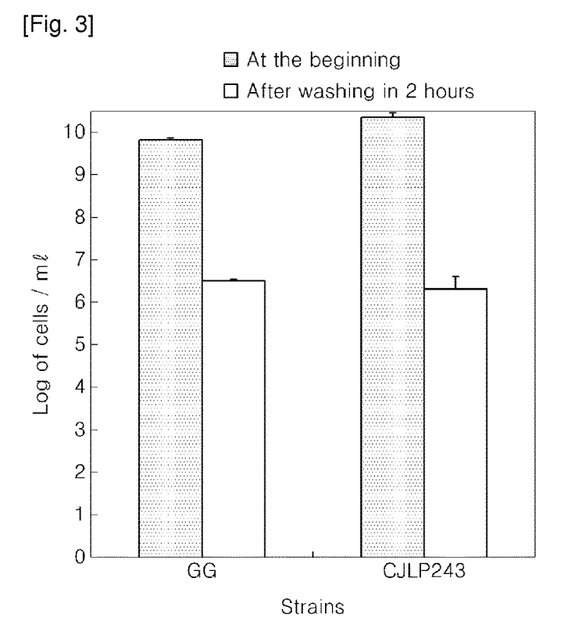
FIG. 3 is a graph illustrating an ability of *Lactobacillus plantarum* CJLP243 to adhere to intestinal epithelial cells.

The results are shown in FIG. 3. FIG. 3 is a graph illustrating an adhesion ability of *Lactobacillus plantarum* CJLP243 to intestinal epithelial cells.

Referring to FIG. 3. *Lactobacillus plantarum* CLJP243 had a greater adhesion ability to intestinal epithelial cells after 24 hours compared to *Lactobacillus rhamnosus* GG (KCTC 503) commercially well known as a probiotic. According to these results. it can be seen that the *Lactobacillus plantarum* CLJP243 according to one aspect of the present invention is capable of adhering to intestinal epithelial cells, thereby improving intestinal environments.

Example 4: Safety Test of *Lactobacillus plantarum* CJLP243 Strains

In order to evaluate safety of the strains isolated in Example 1, a hemolysis test, a gelatin liquefaction test, a hazardous metabolite (ammonia) formation test, and a phenylalanine deaminase test were conducted according to safety test methods suggested by a collective standard of the Korean Bio Venture Association.

The results are shown in Table 2 below.

TABLE 2

Safety Test of *Lactobacillus plantarum* CJLP243 Strains

| Strains | Test | | | |
|---|---|---|---|---|
| | gelatin liquefaction test | phenylalanine deaminase test | hemolysis test | ammonia formation test |
| CJLP243 | negative | negative | α-hemolysis, safe | negative |

According to the results, *Lactobacillus plantarum* CJLP243 was negative for the gelatin liquefaction test, the hazardous metabolite (ammonia) formation test, and the phenylalanine deaminase test, and showed α-hemolysis which is estimated not to be related to a pathogen. Thus, it was proven that *Lactobacillus plantarum* CJLP243 can be safely administered to the human body.

Example 5: The Growth of Mouse Immune Cell by Way of Ex Vivo Experiment

In order to identify the immune enhancing ability of *Lactobacillus plantarum* CJLP243, the growth of mouse immune cells was identified by an MIT assay. The MTT assay was conducted as follows according to the manufacturer's instructions of an MTT assay kit (promega, cat number G5430). First, immune cells obtained by eliminating blood cells from splenocytes of a B6 mouse were diluted in a RPMI 1640 medium containing 10% fetal bovine serum. Afterwards, the immune cells were seeded into the 96-well plate in the number of $1 \times 10^6$ cells/well (total volume 200 μl). After the seeding of the immune cells was completed, live *Lactobacillus plantarum* CJLP 243 ($5 \times 10^6$ cells) were added to each well and cultured at 37° C. in a 5% $CO_2$ incubator for 3 days. After 3 days, 100 μl of medium was removed 1 hour before the MIT assay in order to prepare for the MTT assay. Then, 20 μl of MTT solution (2 mg/ml) was dispensed into each well, and then cultured at 37° C. for 1 hour. Afterwards, absorbance was measured at 490 nm using an ELISA reader (Molecular device, USA). This procedure was repeated at least 3 times. In this procedure, positive control groups, each at a concentration of 10 μg/ml, used concanavalin A (con A; sigma cat number L6397), phytohemaglutamine (PHA; sigma cat number L8902), or lipopolysaccharide (LPS; sigma cat number L4516) which are main mitogens. Furthermore, 99% pure β-glucan was purchased from Sigma Chemical (cat number G5011, USA) and was used in the final concentration of 1.25 μg/ml to compare the immune enhancing ability. The results are shown at FIG. 4.

Figure 4:
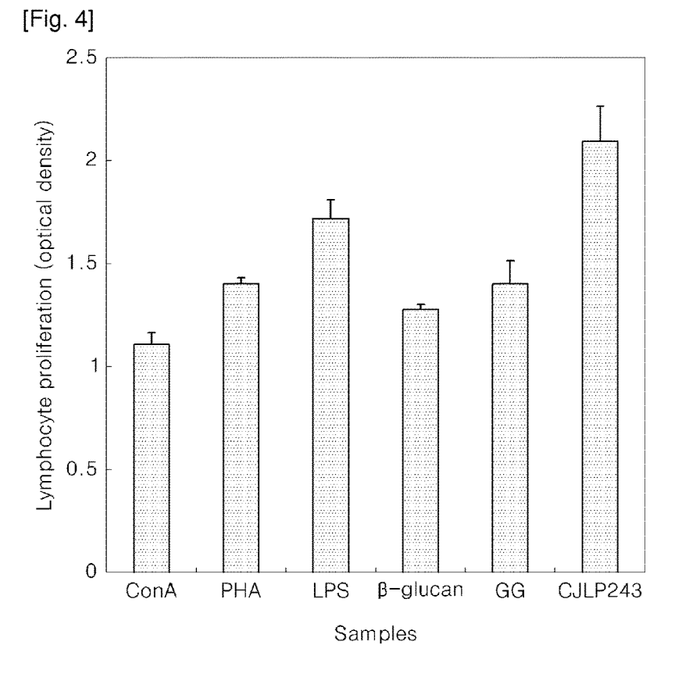
FIG. 4 is a graph illustrating the results of a MTT assay which was conducted on immune cells from a spleen, which were isolated from mice and cultured ex vivo, and then treated with *Lactobacillus plantarum* CJLP243, in comparison with main mitogen treatment groups, a β-glucan treatment group and a *Lactobacillus rhamnosus* GG treatment group.

FIG. 4 is a graph illustrating the results of the MTT assay which was conducted on immune cells from a spleen, which were isolated from a mouse and cultured ex vivo, and then treated with *Lactobacillus plantarum* CJLP243.

Referring to FIG. 4, it can be said that *Lactobacillus plantarum* CJLP243 has superior ability to activate splenocyte growth compared to the main mitogens, β-glucan, and *Lactobacillus rhamnosus* GG (KCTC 5033), and thus is confirmed to be able to induce the enhanced immunity.

Example 6: Ability of Producing IFN-γ Using Cytokine Assay

In order to identify an immune enhancing ability of *Lactobacillus plantarum* CJLP243 on a foreign antigen, the production ability of IFN-γ, a Th1-type cytokine, was measured using an ELISA assay. First, immune cells obtained by eliminating blood cells from splenocytes of a B6 mouse were diluted in a RPMI 1640 medium containing 10% fetal bovine serum. Afterwards, the immune cells were seeded into the 96-well plate in the number of $1 \times 10^6$ cells/well (total volume 200 μl). After the seeding of the immune cells was completed, live *Lactobacillus plantarum* CJLP 243 ($5 \times 10^5$ cells) were added to each well and cultured at 37° C. in a 5% $CO_2$ incubator for 3 days. After 3 days, 50 μl of the culture medium was removed and the amount of IFN-γ contained therein was measured using the ELISA assay. In order to conduct the ELISA assay, an ELISA plate was coated with an IFN-γ antibody at room temperature for 4 hours, and then the culture medium 50 μl were added thereto and cultured at room temperature. Afterwards, the culture medium was eliminated from the ELISA plate, which was then coated with a biotinylated IFN-γ antibody (BD Bioscience, cat number 554410), which is a second antibody, at room temperature for about 2 hours. Color reaction was induced by streptavidine-conjugated horseradish peroxidase (vectore, cat number SA-5004) and its substrate, TMB (3,3',5, 5'-tetramethylbenzidine, KPL, cat number 50-76-03). After the color reaction was conducted, 100 μg/ml of stop solution (3M HCl) was added to the plate in order to stop the color reaction. At this time, the color reaction showed the color change from blue to yellow, and the absorbance was measured at 450 nm using an ELISA reader (Molecular device, USA) after the color reaction stopped. This procedure was repeated at least 3 times. In these procedures, positive control groups used concanavalin A (con A; sigma cat number L6397), phytohemaglutamine (PHA; sigma cat number L8902), or lipopolysaccharide (LPS; sigma cat number L4516) which are main mitogens, each in the concentration of 10 μg/ml. Further, 99% pure β-glucan was purchased from Sigma Chemical (cat number G5011, USA) and used in an amount of 1.25 mg in the final to compare the immune enhancing ability. The results are shown at FIG. 5.

Figure 5:
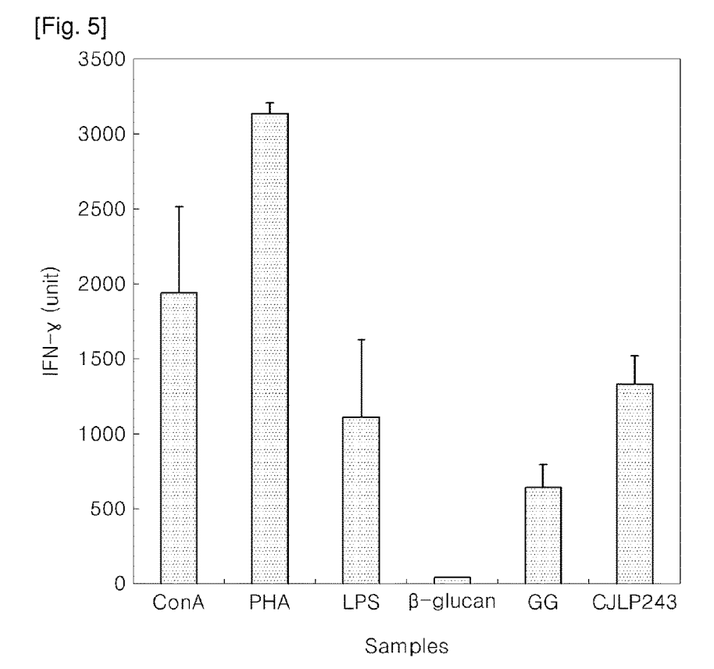
FIG. 5 is a graph illustrating the results of an IFN-γ assay, which was conducted on immune cells from a spleen which were isolated from mice and cultured ex vivo, and then treated with *Lactobacillus plantarum* CJLP243, in comparison with a main mitogen treatment group, a β-glucan treatment group and a *Lactobacillus rhamnosus* GG treatment group.

FIG. 5 is a graph illustrating the results of the IFN-γ assay which was conducted on the immune cells from the spleen which were isolated from the mouse and cultured ex vivo, and then treated with *Lactobacillus plantarum* CJLP243.

Referring to FIG. 5, it can be said that *Lactobacillus plantarum* CJLP243 has inferior ability to the main mitogens that are positive control groups, but significantly superior ability to *Lactobacillus rhamnosus* GG (KCTC 5033) with respect to the IFN-γ production, and thus is confirmed to be able to induce the enhanced Th1-type immunity.

Example 7: Enhanced Immunity of *Lactobacillus plantarum* CJLP243 Strain when it is Orally Administered A test for identifying the enhanced immunity of a *Lactobacillus plantarum* CJLP243 strain when it is orally administered was conducted as follows.

4-week-old female Balb/c mice were purchased and maintained for stabilization for 1 week in an animal breeding room, which was in the SPF condition maintained at a temperature of 24±2° C. and a humidity of 55±15%. The mice were provided with general powdered livestock feed to which some antibiotics were added, and were provided with water ad libitum. Each *Lactobacillus rhamnosus* GG and *Lactobacillus plantarum* CJLP 243 was processed in the form of lyophilized powder, which was kepi refrigerated. Lactic acid bacteria was uniformly mixed with powdered livestock feed and orally administered to the mice at a dose of 2.5×10$^{10}$ CFU/day/mouse. The weight of each mouse was measured for 8 weeks during the administration, and then all the mice were killed for the following experiments.

The spleen was removed from each killed mouse, and its length and weight were measured. The spleen was smashed using a plunger of a syringe and filtered through a mesh in order to separate cells, and these processes were conducted in an ACK buffer. The separated cells were counted using a microscope.

In order to identify the composition change of immune cells in the separated splenocytes, T cells in separated cells were stained with anti-Thy1.2-FITC antibodies, and B cells were stained with anti-CD19-FITC antibodies. CD T cells were stained with anti-Thy1.2-FITC antibodies and anti-CD4-PE antibodies, and CD8 cells were stained with anti-Thy1.2-FITC antibodies and anti-CD8-PE antibodies. Stained cells in each tissue were analyzed for their composition ratio using a FACScan (BD Biosciences, USA).

The separated splenocytes were treated with ConA at the concentration of 5 µg/mL to stimulate T lymphocytes. After 24 hours, the supernatant was removed and measured for the concentrations of IFN-γ and IL-2, T lymphocyte cytokines, using an ELISA. A microplate was coated with IFN-γ and IL-2 capture antibodies at 4° C. overnight, and then washed with PBS (PBST) containing 0.05% Tween20 and blocked with PBS containing 3% fetal bovine serum. After 1 hour, the microplate was washed and the supernatant and a standard solution (a standard solution provided by BD Bioscience) were added to each well and reacted at 4° C. overnight. Then, the microplate was washed and biotinylated antibodies were added to each well, and the reaction was conducted at room temperature for 45 minutes. Afterwards, the microplate was washed and streptavidine-alkaline phosphatase was added to each well, and culturing was conducted at room temperature for 30 minutes. After washing the microplate, a color reaction was conducted by adding a p-nitrophenyl phosphate (Sigma, USA) solution to each well. Absorbance was measured at 405 nm using a microplate reader, and the concentration of cytokines was measured using a standard curve.

The results are shown in FIGS. 6 to 11.

Figure 6:
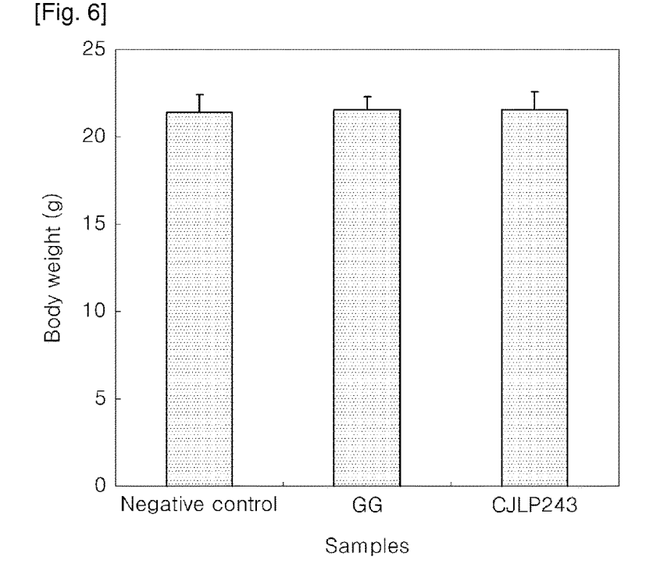
FIG. 6 is a graph illustrating a body weight measured just before killing mice orally administered with *Lactobacillus plantarum* CJLP243 strains, in comparison with a negative control group and a *Lactobacillus rhamnosus* GG administration group.

FIG. 6 is a graph illustrating the weight measured just before killing the mice orally administered with *Lactobacillus plantarum* CJLP243 strains, in comparison with a negative control group and a *Lactobacillus rhamnosus* GG administration group.

Referring to FIG. 6, a *Lactobacillus plantarum* CJLP243 strains administration group was seen to maintain normal body weight without any abnormalities due to excessive enhanced immunity, and no abnormalities were observed with respect to the weight of the spleen and the number of cells (data is not shown).

Figure 7:
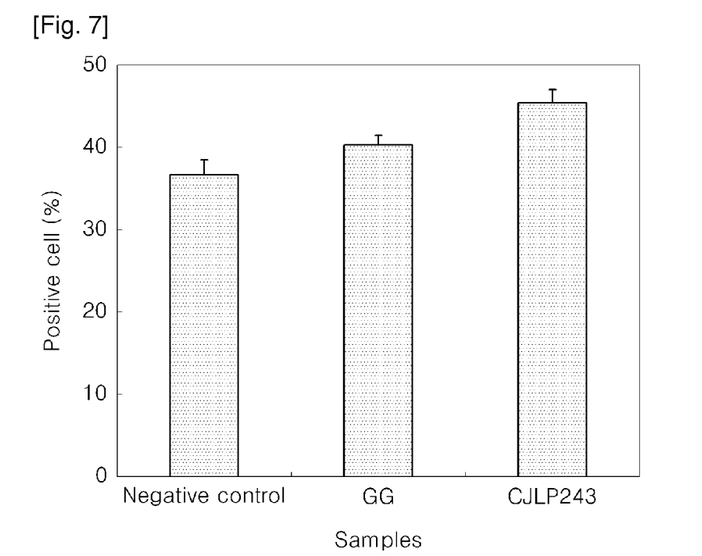
FIG. 7 is a graph illustrating results obtained by measuring a change in T cell population in order to identify the effect of *Lactobacillus plantarum* CJLP243 strains on immune cells in the spleen isolated after killing the mice orally administered with *Lactobacillus plantarum* CJLP243 strains, in comparison with a negative control group and a *Lactobacillus rhamnosus* GG administration group.

FIG. 7 is a graph illustrating the results obtained by measuring the change in a T cell population in order to identify the effect of *Lactobacillus plantarum* CJLP243 strains on the immune cells in the spleen isolated after killing the mice orally administered with *Lactobacillus plantarum* CJLP243 strains, in comparison with a negative control group and a *Lactobacillus rhamnosus* GG administration group.

Figure 8:
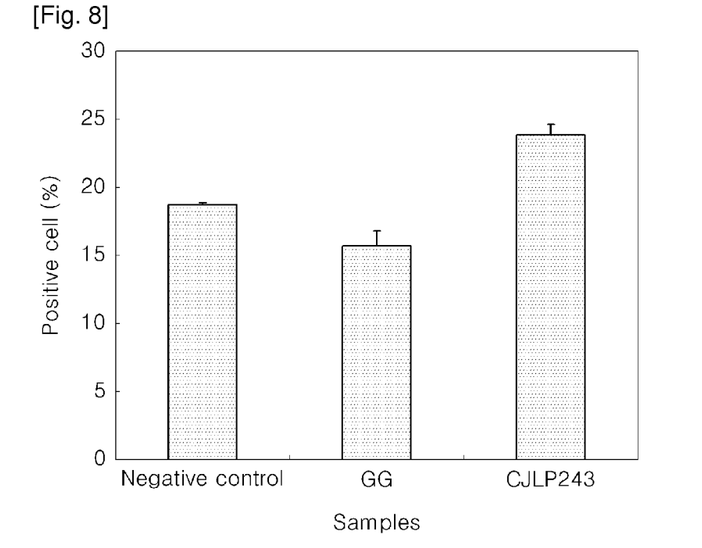
FIG. 8 is a graph illustrating results obtained by measuring a change in CD4 T cell population in order to identify the effect of *Lactobacillus plantarum* CJLP243 strains on the immune cells in the spleen isolated after killing the mice orally administered with *Lactobacillus plantarum* CJLP243 strains, in comparison with a negative control group and a *Lactobacillus rhamnosus* GG administration group.

FIG. 8 is a graph illustrating the results obtained by measuring the change in a CD4 T cell population in order to identify the effect of *Lactobacillus plantarum* CJLP243 strains on the immune cells in the spleen isolated after killing the mice orally administered with *Lactobacillus plantarum* CJLP243 strains, in comparison with a negative control group and a *Lactobacillus rhamnosus* GG administration group.

Figure 9:
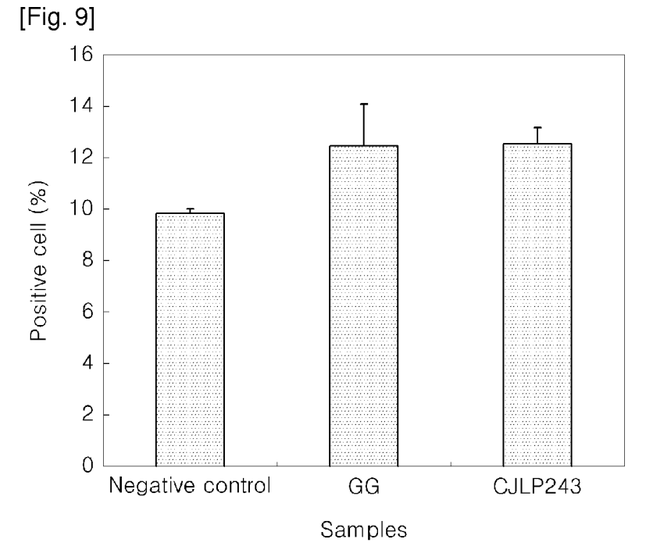
FIG. 9 is a graph illustrating results obtained by measuring a change in CD8 T cell population in order to identify the effect of *Lactobacillus plantarum* CJLP243 strains on the immune cells in the spleen isolated after killing the mice orally administered with *Lactobacillus plantarum* CJLP243 strains, in comparison with a negative control group and a *Lactobacillus rhamnosus* GG administration group.

FIG. 9 is a graph illustrating the results obtained by measuring the change in a CD8 T cell population in order to identify the effect of *Lactobacillus plantarum* CJLP243 strains on the immune cells in the spleen isolated after killing the mice orally administered with *Lactobacillus plantarum* CJLP243 strains, in comparison with a negative control group and a *Lactobacillus rhamnosus* GG administration group.

Referring to FIGS. 7, 8 and 9, *Lactobacillus plantarum* CJLP243 strains are identified to increase the number of T cells, CD4 T cells, and CD8 T cells, and thus it can be said that *Lactobacillus plantarum* CJLP243 enhances immunity by affecting the activation of T cell growth.

Additionally, in order to identify the effect of *Lactobacillus plantarum* CJLP243 on the activation of T cells, the amount of IL-2 and IFN-γ produced by T cells from spleen cells which were obtained from the spleen isolated after killing the mice orally administered with *Lactobacillus plantarum* CJLP243 strains and then stimulated with ConA ex vivo, were measured using the ELISA method. The obtained results are shown in FIGS. 10 and 11.

Figure 10:
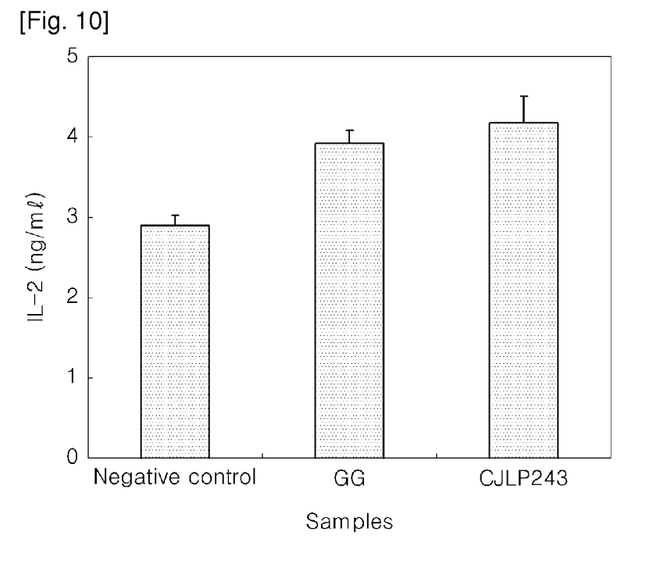
FIG. 10 is a graph illustrating results obtained by measuring the amount of IL-2 produced by T cells from spleen cells which were obtained from the spleen isolated after killing the mice orally administered with *Lactobacillus plantarum* CJLP243 strains and then stimulated with ConA ex vivo, using an enzyme-linked immunosorbent assay (ELISA) method, in order to identify the effect of *Lactobacillus plantarum* CJLP243 on the activation of cells, in comparison with a negative control group and a *Lactobacillus rhamnosus* GG administration group.

FIG. 10 is a graph illustrating the results obtained by measuring the amount of IL-2 produced by T cells from spleen cells which were obtained from the spleen isolated after killing the mice orally administered with *Lactobacillus plantarum* CJLP243 strains and then stimulated with ConA ex vivo, using the ELISA method, in order to identify the effect of *Lactobacillus plantarum* CJLP243 on the activation of T cells, in comparison with a negative control group and a *Lactobacillus rhamnosus* GG administration group.

Figure 11:
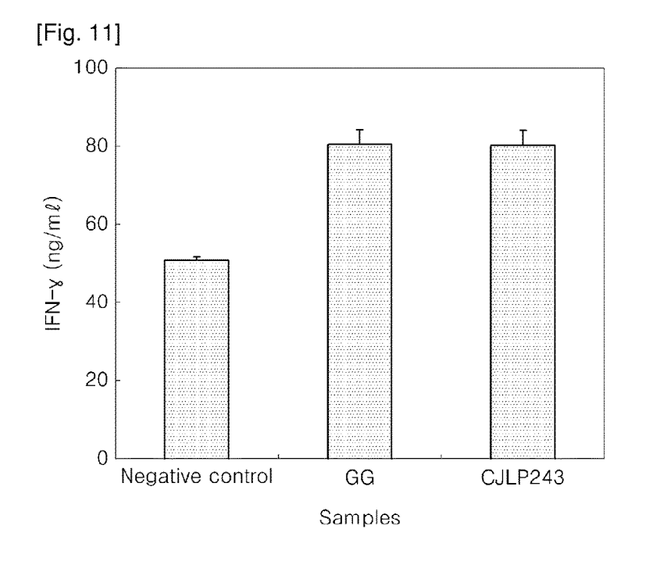
FIG. 11 is a graph illustrating the results obtained by measuring the amount of IFN-γ. produced by cells from spleen cells which were obtained from the spleen isolated after killing the mice orally administered with *Lactobacillus plantarum* CJLP243 strains and then stimulated with ConA ex vivo, using the ELISA method, in order to identify the effect of *Lactobacillus plantarum* CJLP243 on the activation of T cells, in comparison with a negative control group and a *Lactobacillus rhamnosus* GG administration group.

FIG. 11 is a graph illustrating the results obtained by measuring the amount of IFN-γ produced by T cells from spleen cells which were obtained from the spleen isolated after killing the mice orally administered with *Lactobacillus plantarum* CJLP243 strains and then stimulated with ConA ex vivo, using the ELISA method, in order to identify the effect of *Lactobacillus plantarum* CJLP243 on the activation of T cells, in comparison with a negative control group and a *Lactobacillus rhamnosus* GG administration group.

Referring to FIGS. 10 and 11, it can be said that *Lactobacillus plantarum* CJLP243 strains are identified to increase the production of T cell cytokines over the negative control group, by which *Lactobacillus plantarum* CJLP243 may induce the activation of T cells and enhance general immunity.

Example 8: Preparation of Probiotics Powder Comprising *Lactobacillus plantarum* CJLP243

*Lactobacillus plantarum* CJLP243 identified in Example 1 were mass-produced and lyophilized to make probiotics to be applied to raw materials for pharmaceuticals, food, livestock feed, livestock feed additives, or cosmetics.

The bacteria were incubated in a liquid MRS medium (Difco) at 37° C. for 18 hours while regulating the pH at 6.0 using a 25% NaOH solution, and centrifuged to obtain strains. The collected strains were lyophilized at −40° C. using 5% dextrin and 10% skim milk as lyophilization protecting agents, and the dried strains were pulverized using a mixer at 37° C. to prepare powder. The powdered live bacteria were mixed with excipients, such as glucose, lactic acid, and skim milk, to adjust the number of bacteria to a desired level and to store the live bacteria, and packed in a sealed aluminum pouch.

The probiotics prepared according to this method may be applied to pharmaceuticals, food, livestock feed, cosmetics, or the like, by being mixed with grain powder used as a raw material of the livestock feed, by being mixed with excipients or additives to form pharmaceuticals, such as tablets and capsules, or food, and by being mixed with raw materials to form cosmetics.

While the present invention has been particularly shown and described with reference to exemplary embodiments thereof, it will be understood by those of ordinary skill in the art that various changes in form and details may be made therein without departing from the spirit and scope of the present invention as defined by the following claims.

The invention claimed is:

1. A bacterial composition, comprising:
   *Lactobacillus plantarum* CJLP243 strain KCCM 11045P and
   an effective amount of a lyophilization protecting agent, wherein the bacterial composition is a freeze-dried composition.

2. The bacterial composition of claim 1, wherein the cryoprotectant is selected from the group consisting of skim milk and dextrin.

3. A pharmaceutical composition, comprising the bacterial composition of claim 1 and a suitable pharmaceutically acceptable excipient or additive.

4. The pharmaceutical composition of claim 3, wherein a formulation of the pharmaceutical composition is selected from the group consisting of liquids, suspensions, powder, granules, tablets, capsules, pills and extracts.

5. A food composition, comprising the bacterial composition of claim 1 and a food.

6. The food composition of claim 5, further comprising sitologically acceptable excipient or additive.

7. A livestock feed composition, comprising the bacterial composition of claim 1 and a livestock feed.

8. A livestock feed additive, comprising the bacterial composition of claim 1 and an organic acid or a natural antioxidant.

9. A cosmetic, comprising the bacterial composition of claim 1 and a cosmetic excipient or additive.

10. The composition of claim 1, suitable for use in treatment of intestinal disease.

11. The composition of claim 10, wherein the intestinal disease is selected from the group consisting of infectious diarrhea caused by pathogenic microorganisms, gastroenteritis, inflammatory bowel disease, psychogenic enteritis syndrome, overgrowth of microorganisms in the small intestine and diarrhea.

12. The composition of claim 1, suitable for use in treatment of immune disease.

13. The composition of claim 12, wherein the immune disease is selected from the group consisting of allergic diseases, atopy, cancer and autoimmune diseases.

* * * * *

SEQUENCE LISTING

<160> NUMBER OF SEQ ID NOS: 1

<210> SEQ ID NO 1
<211> LENGTH: 1461
<212> TYPE: DNA
<213> ORGANISM: Lactobacillus plantarum

<400> SEQUENCE: 1

```
agtcgaacga actctggtat tgattggtgc ttgcatcatg atttacattt gagtgagtgg      60
cgaactggtg agtaacacgt gggaaacctg cccagaagcg ggggataaca cctggaaaca     120
gatgctaata ccgcataaca acttggaccg catggtccga gcttgaaaga tggcttcggc     180
tatcactttt ggatggtccc gcggcgtatt agctagatgt tggggtaacg gctcaccatg     240
gcaatgatac gtagccgacc tgagagggta atcggccaca ttgggactga gacacggccc     300
aaactcctac gggaggcagc agtagggaat cttccacaat ggacgaaagt ctgatggagc     360
aacgccgcgt gagtgaagaa gggtttcggc tcgtaaaact ctgttgttaa agaagaacat     420
atctgagagt aactgttcag gtattgacgg tatttaacca gaaagccacg gctaactacg     480
tgccaacagc cgcggtaata cgtaggtggc aagcgttgtc cggatttatt gggcgtaaag     540
cgagcgcagg cggtttttta aatctgatgt gaaagccttc ggctcaaccg aagaagtgca     600
tcggaaactg ggaaacttga gtgcagaaaa agacaatgga actccatgtg tagcggtgaa     660
aatgcgtaat atatggaaga acaccagtgg cgaaggcggc tgtctggtct gtaactgacg     720
ctgaggctcg aaagtatggg tagcaaacag gattagatac cctggtagtc cataccgtaa     780
acgatgaatg ctaagtgttg gagggtttcc gcccttcagt gctgcagcta acgcattaag     840
cattccgcct ggggagtacg gccgcaaggc tgaaactcaa aggaattgac ggggcccgc      900 acaagcggtg gagcatgtgg tttaattcga agctacgcga agaaccttac caggtcttga     960
catactatgc aaatctaaga gattagacgt tcccttcggg gacatggata caggtggtgc    1020
atggttgtcg tcagctcgtg tcgtgagatg ttgggttaag tcccgcaacg agcgcaaccc    1080
ttattatcag ttgccagcat taagttgggc actctggtga gactgccggt gacaaaccgg    1140
aggaaggtgg ggatgacgtc aaatcatcat gccccttatg acctgggcta cacacgtgct    1200
acaatggatg gtacaacgag ttgcgaactc gcgagagtaa gctaatctct aaagccatt     1260 ctcagttcgg attgtaggct gcaactcgcc tacatgaagt cggaatcgct agtaatcgcg    1320
gatcagcatg ccgcggtgaa tacgttcccg ggccttgtac acaccgcccg tcacaccatg    1380
agagtttgta acacccaaag tcggtggggt aaccttttag gaaccagccg cctaaggtgg    1440
gacagatgat tagggtgaag t                                              1461
```